US006899931B2

United States Patent
Porchia et al.

(10) Patent No.: US 6,899,931 B2
(45) Date of Patent: May 31, 2005

(54) FILM MATERIAL

(75) Inventors: Jose Porchia, Milwaukee, WI (US); Julie M. Grissmeyer, Racine, WI (US); Frederick H. Martin, Racine, WI (US); Pamela J. Taylor, Mt. Pleasant, WI (US)

(73) Assignee: S. C. Johnson Home Storage, Inc., Racine, WI (US)

( * ) Notice: Subject to any disclaimer, the term of this patent is extended or adjusted under 35 U.S.C. 154(b) by 0 days.

(21) Appl. No.: 09/948,211

(22) Filed: Sep. 7, 2001

(65) Prior Publication Data

US 2003/0049394 A1 Mar. 13, 2003

(51) Int. Cl.[7] .............................................. B32B 27/14
(52) U.S. Cl. ................... 428/35.7; 428/36.92; 428/905
(58) Field of Search ............................ 428/35.7, 36.92, 428/905

(56) References Cited

U.S. PATENT DOCUMENTS

| 339,810 A | 4/1886 | Regan | |
|---|---|---|---|
| 1,151,895 A | 8/1915 | Mix | |
| 1,952,375 A | 3/1934 | Johnson | 107/46 |
| 2,169,055 A | 8/1939 | Overshiner | 167/94 |
| 2,369,898 A | 2/1945 | Hoel | 107/46 |
| 2,720,013 A | 10/1955 | Clarke | 21/126 |
| 2,956,073 A | 10/1960 | Whetstone et al. | 160/461 |
| 3,044,885 A | 7/1962 | Loehr et al. | 99/154 |
| 3,116,201 A | 12/1963 | Whetstone et al. | 167/22 |
| 3,120,345 A | 2/1964 | Bolger | 239/52 |

(Continued)

FOREIGN PATENT DOCUMENTS

| AU | 91 88 250 | 11/1991 |
|---|---|---|
| AU | A-88250/91 | 5/1992 |
| CN | 1 056 911 | 12/1991 |
| CN | 1993-00117205 | 9/1993 |
| DE | Nr. 242 632 | 1/1911 |
| DE | Nr. 187 035 | 10/1936 |
| DE | Nr. 1 776 511 | 10/1958 |
| DE | 1 042 851 | 11/1958 |
| DE | 1 230 259 | 12/1966 |
| DE | 1 935 405 | 7/1969 |

(Continued)

OTHER PUBLICATIONS

XP002149732, Derwent Publications Ltd., London, Great Britain (May 28, 1998).
Chemical Abstracts, vol. 100, No. 21, Abstract No. 169902; Abstract of Masachika et al.
Database WPI, Section CH, Week 8136, Derwent Publications Ltd., London GB; Class C03, AN 81–65092D; Derwent Abstract for JP,A,56 090 004 (Earth Seiyaku KK).
Patent Abstracts of Japan, vol. 12, No. 344; Abstract of Fumitoshi, JP,A,63 101 301.
Patent Abstracts of Japan, vol. 13, No. 556 (C–664); Abstract for JP,A,01 230 502 (Fumakilla).
Chemical Abstracts, vol. 117, No. 1, Abstract No. 2831; Abstract for Peop. Rep. of China Patent, Cui, CN 1056911A.
Database WPI, Section CH, Week 9013, Derwent Publications Ltd., London, GB; Class C03, An 90–096004; Derwent Abstract for JP,A,02 048 507 (Sumitomo Chem. Ind. KK).
Pflanzenschutz Nachrichten Bayer (Special Edition), Published by Bayer AG, Copyright 1995 by Bayer AG, Leverkusen.
International Search Report dated Nov. 20, 2002, International Application No. PCT/US02/28423.

(Continued)

Primary Examiner—Sandra M. Nolan

(57) ABSTRACT

A material includes a first film layer that carries an electric charge, a second film layer secured to the first film layer to form a pocket and a volatile substance disposed in the pocket.

7 Claims, 5 Drawing Sheets

U.S. PATENT DOCUMENTS

| | | | |
|---|---|---|---|
| 3,240,326 A | 3/1966 | Miller | 206/46 |
| 3,261,746 A | 7/1966 | Copley | 167/42 |
| 3,295,246 A | 1/1967 | Landsman et al. | 43/131 |
| 3,318,769 A | 5/1967 | Folckemer et al. | 167/42 |
| 3,458,713 A | 7/1969 | Perlman et al. | 307/88 |
| 3,567,119 A | 3/1971 | Wilbert | 239/6 |
| 3,576,987 A | 5/1971 | Voight | 240/2.25 |
| 3,620,453 A | 11/1971 | Gancberg et al. | 239/60 |
| 3,644,605 A | 2/1972 | Sessler et al. | 364/22 |
| 3,655,129 A | 4/1972 | Seiner | 239/60 |
| 3,660,736 A | 5/1972 | Igarashi et al. | 317/262 F |
| 3,685,734 A | 8/1972 | Paciorek et al. | 239/56 |
| 3,685,895 A | 8/1972 | Wright et al. | 399/169 |
| 3,734,486 A | 5/1973 | Peacey | 269/302.1 |
| 3,794,986 A | 2/1974 | Murayama | 340/173 CH |
| 3,804,077 A | 4/1974 | Williams | 126/263.1 |
| 3,857,934 A | 12/1974 | Bernstein et al. | 424/30 |
| 3,864,468 A | 2/1975 | Hyman et al. | 424/16 |
| 3,874,504 A | 4/1975 | Verakas | 206/219 |
| 3,876,762 A | 4/1975 | Rabussier et al. | 424/78 |
| 3,910,410 A | 10/1975 | Shaw | 206/363 |
| 3,985,666 A | 10/1976 | Ciccarelli et al. | 252/63.2 |
| 3,994,439 A | 11/1976 | Van Breen et al. | 239/54 |
| 4,051,159 A | 9/1977 | Tsoucalas et al. | 260/404.5 |
| 4,057,047 A | 11/1977 | Gossett | 126/263.07 |
| 4,086,499 A | 4/1978 | Mishra | 307/88 ET |
| 4,094,119 A | 6/1978 | Sullivan | 53/4 |
| 4,103,450 A | 8/1978 | Whitcomb | 43/131 |
| 4,128,508 A | 12/1978 | Munden | 252/522 |
| 4,145,001 A | 3/1979 | Weyenberg et al. | 239/56 |
| 4,158,440 A | 6/1979 | Sullivan et al. | 239/1 |
| 4,164,178 A | 8/1979 | Baumann et al. | 100/99 |
| 4,173,659 A | 11/1979 | Dubois et al. | 427/35 |
| 4,178,384 A | 12/1979 | Ensing, deceased | 424/16 |
| 4,207,702 A | 6/1980 | Boatman et al. | 46/74 |
| 4,225,369 A | 9/1980 | Felchlin | 156/71 |
| 4,275,112 A | 6/1981 | Savage, Jr. | 428/310 |
| 4,288,584 A | 9/1981 | Mishra | 526/348.4 |
| 4,291,245 A | 9/1981 | Nowlin et al. | 307/400 |
| 4,348,439 A | 9/1982 | Jones | 428/36 |
| 4,407,852 A | 10/1983 | Sapieha et al. | 427/41 |
| 4,439,415 A | 3/1984 | Hennart et al. | 424/16 |
| 4,445,641 A | 5/1984 | Baker et al. | 239/6 |
| 4,459,634 A | 7/1984 | Stefanou | 361/233 |
| 4,461,808 A | 7/1984 | Mollison | 428/475.8 |
| 4,475,663 A | 10/1984 | Kittscher et al. | 220/87 |
| 4,493,869 A | 1/1985 | Sweeny et al. | 428/201 |
| 4,504,550 A | 3/1985 | Pook | 428/461 |
| 4,513,049 A | 4/1985 | Yamasaki et al. | 428/194 |
| 4,515,909 A | 5/1985 | Sawano et al. | 523/102 |
| 4,534,509 A | 8/1985 | Holzner | 239/34 |
| 4,557,377 A | 12/1985 | Maloney | 206/219 |
| 4,598,531 A | 7/1986 | Ruff et al. | 53/461 |
| 4,626,263 A | 12/1986 | Inoue et al. | 55/155 |
| 4,631,231 A | 12/1986 | Stendel et al. | 428/413 |
| 4,678,684 A | 7/1987 | Sand | 427/213.36 |
| 4,696,844 A | 9/1987 | Spector | 428/46 |
| 4,717,017 A | 1/1988 | Sprinkel, Jr. et al. | 206/264 |
| 4,720,409 A | 1/1988 | Spector | 428/46 |
| 4,720,417 A | 1/1988 | Sweeny et al. | 428/201 |
| 4,741,119 A | 5/1988 | Baryla | 40/594 |
| 4,752,496 A | 6/1988 | Fellows et al. | 427/27 |
| 4,765,982 A | 8/1988 | Ronning et al. | 424/403 |
| 4,780,117 A | 10/1988 | Lahey et al. | 62/4 |
| 4,786,353 A | 11/1988 | Templeton et al. | 156/359 |
| 4,796,381 A | 1/1989 | Kauth et al. | 43/124 |
| 4,804,142 A | 2/1989 | Riley | 239/56 |
| 4,808,454 A | 2/1989 | Saitoh | 428/42 |
| 4,814,212 A | 3/1989 | Spector | 428/14 |
| 4,824,707 A | 4/1989 | Spector | 428/46 |
| 4,856,651 A | 8/1989 | Francis, Jr. | 206/219 |
| 4,860,488 A | 8/1989 | Shigetoyo | 43/129 |
| 4,865,855 A | 9/1989 | Hansen et al. | 426/124 |
| 4,879,117 A | 11/1989 | Rombi | 424/411 |
| 4,880,690 A | 11/1989 | Szycher et al. | 428/224 |
| 4,884,680 A | 12/1989 | Israel et al. | 206/44.11 |
| 4,900,876 A | 2/1990 | Bushman et al. | 119/106 |
| 4,901,674 A | 2/1990 | Bushman et al. | 119/106 |
| 4,908,252 A | 3/1990 | Carnahan et al. | 428/27 |
| 4,925,517 A | 5/1990 | Charbonneau et al. | 156/276 |
| 4,940,729 A | 7/1990 | Matthewson | 514/521 |
| 4,966,796 A | 10/1990 | Aki et al. | 428/34.3 |
| 4,981,938 A | 1/1991 | Hanari et al. | 526/351 |
| 4,988,557 A | 1/1991 | Charbonneau | 428/204 |
| 4,990,381 A | 2/1991 | Holzner | 428/35.3 |
| 4,992,121 A | 2/1991 | Rubino | 156/71 |
| 5,010,671 A | 4/1991 | Stonehouse | 40/594 |
| 5,015,476 A | 5/1991 | Cochrum et al. | 424/423 |
| 5,024,898 A | 6/1991 | Pitts et al. | 428/511 |
| 5,031,975 A | 7/1991 | Anderson | 312/319 |
| 5,037,702 A | 8/1991 | Pitts et al. | 428/423.7 |
| 5,057,588 A | 10/1991 | East et al. | 526/300 |
| 5,057,710 A | 10/1991 | Nishiura et al. | 307/400 |
| 5,071,704 A | 12/1991 | Fischel-Ghodsian | 428/354 |
| 5,085,416 A | 2/1992 | Miyake et al. | 269/289 R |
| 5,091,183 A | 2/1992 | Yano et al. | 424/405 |
| 5,102,171 A | 4/1992 | Saetre | 283/117 |
| 5,156,843 A | 10/1992 | Leong et al. | 424/411 |
| 5,186,707 A | 2/1993 | Barta | 493/439 |
| 5,193,793 A | 3/1993 | Pollock | 269/302.1 |
| 5,198,287 A | 3/1993 | Samson et al. | 428/248 |
| 5,207,581 A | 5/1993 | Boyd | 434/412 |
| 5,227,172 A | 7/1993 | Deeds | 425/72.2 |
| 5,229,122 A | 7/1993 | Chadwick et al. | 424/408 |
| 5,231,144 A | 7/1993 | Yamamoto et al. | 525/333.8 |
| 5,249,676 A | 10/1993 | Ashcraft et al. | 206/264 |
| 5,252,387 A | 10/1993 | Samson et al. | 428/248 |
| 5,258,214 A | 11/1993 | Cooledge et al. | 428/43 |
| 5,280,989 A | 1/1994 | Castillo | 296/136 |
| 5,290,770 A | 3/1994 | Matthewson | 514/86 |
| 5,339,609 A | 8/1994 | Cerf | 53/550 |
| 5,354,996 A | 10/1994 | Griffith et al. | 250/364 |
| 5,373,966 A | 12/1994 | O'Reilly | 222/94 |
| 5,439,172 A | 8/1995 | Comyn et al. | 239/34 |
| 5,439,628 A | 8/1995 | Huang | 264/175 |
| 5,455,043 A | 10/1995 | Fischel-Ghodsian | 424/448 |
| 5,456,704 A | 10/1995 | Kilcullen | 607/111 |
| 5,477,784 A | 12/1995 | Floegel | 101/489 |
| 5,480,851 A | 1/1996 | Tsurumi et al. | 502/185 |
| 5,486,411 A | 1/1996 | Hassenboehler, Jr. et al. | 428/286 |
| 5,487,932 A | 1/1996 | Dunshee | 428/68 |
| 5,492,219 A | 2/1996 | Stupar | 206/219 |
| 5,492,696 A | 2/1996 | Price et al. | 424/417 |
| 5,527,022 A | 6/1996 | Gibson | 269/13 |
| 5,534,020 A | 7/1996 | Cheney, III et al. | 607/108 |
| 5,536,982 A | 7/1996 | Mino et al. | 307/400 |
| 5,543,224 A | 8/1996 | Sakai et al. | 428/409 |
| 5,545,197 A | 8/1996 | Bowen | 607/108 |
| 5,582,884 A | 12/1996 | Ball et al. | 428/34.1 |
| 5,610,455 A | 3/1997 | Allen et al. | 307/400 |
| 5,637,401 A | 6/1997 | Berman et al. | 252/315.2 |
| 5,638,249 A | 6/1997 | Rubino et al. | 361/225 |
| 5,686,050 A | 11/1997 | Wadsworth et al. | 422/186.05 |
| 5,750,645 A | 5/1998 | Huang | 528/502 B |
| 5,800,769 A | 9/1998 | Haskett | 264/484 |
| 5,826,851 A | 10/1998 | Arbisi | 248/466 |
| 5,834,386 A | 11/1998 | Cohen | 442/382 |
| 5,862,960 A | 1/1999 | Miller et al. | 222/325 |
| 5,888,604 A | 3/1999 | Evans, Jr. et al. | 428/47 |

| Patent No. | Date | Inventor | Class |
|---|---|---|---|
| 5,899,010 A | 5/1999 | Peck | 40/618 |
| 5,904,985 A | 5/1999 | Ward et al. | 428/411.1 |
| 5,938,185 A | 8/1999 | Kletter | 269/289 R |
| 5,961,043 A | 10/1999 | Samuelson et al. | 239/54 |
| 5,965,235 A | 10/1999 | McGuire et al. | 428/156 |
| 5,968,633 A | 10/1999 | Hamilton et al. | 428/174 |
| 5,970,638 A | 10/1999 | Henley | 40/594 |
| 5,984,294 A | 11/1999 | Bogomolny | 269/289 R |
| 5,989,685 A | 11/1999 | Hockaday | 428/195 |
| RE36,717 E | 5/2000 | Thompson | 426/518 |
| 6,093,413 A | 7/2000 | Matson | 424/403 |
| 6,116,231 A | 9/2000 | Sabin et al. | 126/263.01 |
| 6,143,255 A | 11/2000 | Cowell Senft | 422/186.04 |
| 6,159,325 A | 12/2000 | Graham et al. | 156/250 |
| 6,162,454 A | 12/2000 | Ahr et al. | 424/411 |
| 6,164,478 A | 12/2000 | Cant | 220/62.1 |
| 6,169,081 B1 | 1/2001 | Ishiwatari | 514/65 |
| 6,221,375 B1 | 4/2001 | Howse | 424/417 |
| 6,258,893 B1 | 7/2001 | Okayama et al. | 525/191 |
| 6,284,339 B1 | 9/2001 | Floegel et al. | 428/43 |
| 6,289,889 B1 | 9/2001 | Bell et al. | 126/263.01 |
| 6,341,602 B1 | 1/2002 | Fulcher | 126/263.07 |
| 6,351,928 B2 | 3/2002 | Torre | 53/556 |
| 6,359,239 B1 | 3/2002 | Missler et al. | 177/25.16 |
| 6,360,477 B1 | 3/2002 | Flashinski et al. | 43/131 |
| 6,376,058 B1 | 4/2002 | Schut et al. | 428/220 |
| 6,383,614 B1 | 5/2002 | Carson et al. | 428/206 |
| 6,422,551 B1 | 7/2002 | Brotz | 269/289 R |
| 6,438,965 B1 | 8/2002 | Liao | 62/4 |
| 6,468,635 B1 | 10/2002 | Cowell Senft | 428/195 |
| 6,478,292 B1 | 11/2002 | Sellers | 269/289 |
| 6,534,079 B1 | 3/2003 | Munagavalasa | 424/409 |
| D475,206 S | 6/2003 | Ackerman et al. | D5/57 |
| 6,579,816 B2 | 6/2003 | Lockett | 442/417 |
| 6,582,714 B1 | 6/2003 | Emmrich et al. | 424/409 |
| 6,605,292 B1 | 8/2003 | Ueda et al. | 424/416 |
| 6,660,210 B2 | 12/2003 | Jones et al. | 264/423 |
| 6,663,830 B1 | 12/2003 | Tindall | 422/28 |
| 2002/0012781 A1 | 1/2002 | Beer et al. | |
| 2002/0020485 A1 | 2/2002 | Weder et al. | 156/214 |
| 2002/0064585 A1 | 5/2002 | Christianson et al. | 426/326 |
| 2002/0068163 A1 | 6/2002 | McDuff | 428/314.8 |
| 2002/0102392 A1 * | 8/2002 | Fish et al. | 428/198 |
| 2002/0179884 A1 | 12/2002 | Hoshino et al. | 252/187.1 |
| 2003/0047044 A1 | 3/2003 | Porchia et al. | 83/13 |
| 2003/0047844 A1 | 3/2003 | Porchia et al. | 264/466 |
| 2003/0047845 A1 | 3/2003 | Martin et al. | 264/466 |
| 2003/0049294 A1 | 3/2003 | Porchia et al. | 424/405 |
| 2003/0049410 A1 | 3/2003 | Munagavalasa et al. | 428/137 |
| 2003/0049454 A1 | 3/2003 | Araki et al. | 428/421 |
| 2003/0060350 A1 | 3/2003 | Taylor et al. | 493/324 |

FOREIGN PATENT DOCUMENTS

| | | | |
|---|---|---|---|
| DE | 2 053 869 | 6/1971 | |
| DE | 22 04 911 C2 | 2/1972 | |
| DE | 2 204 911 | 8/1972 | |
| DE | 78 18 669 | 10/1978 | |
| DE | 29 54 480 C1 | 6/1979 | |
| DE | 29 45 655 A1 | 5/1981 | |
| DE | 30 29 476 A1 | 8/1981 | |
| DE | 31 05 247 A1 | 8/1982 | |
| DE | 83 08 421.5 | 9/1983 | |
| DE | 34 21 290 C2 | 6/1985 | |
| DE | 34 21 290 A1 | 6/1985 | |
| DE | 35 35 523 A1 | 5/1986 | |
| DE | 35 11 215 C2 | 10/1986 | |
| DE | 35 11 215 A1 | 10/1986 | |
| DE | 37 23 380 A1 | 4/1988 | |
| DE | 89 03 480.5 | 3/1989 | |
| DE | 39 38 664 | 5/1990 | |
| DE | 43 20 298 A1 | 12/1994 | |
| DE | 195 30 076 | 2/1997 | |
| DE | 198 06 437 | 8/1999 | |
| DE | 199 47 146 | 5/2000 | |
| EP | 0 069 983 B1 | 1/1983 | |
| EP | 0 670 685 B1 | 9/1985 | |
| EP | 0 169 839 B1 | 2/1986 | |
| EP | 0 253 640 | 1/1988 | |
| EP | 0 301 810 A2 | 2/1989 | C09J/7/02 |
| EP | 0 363 033 | 4/1990 | |
| EP | 0 378 685 | 7/1990 | |
| EP | 0 439 504 B1 | 8/1991 | |
| EP | 0 477 676 | 4/1992 | |
| EP | 0 659 815 A1 | 12/1993 | C08K/5/18 |
| EP | 0 594 892 B1 | 5/1994 | |
| EP | 0 596 317 | 5/1994 | |
| EP | 0 702 052 A1 | 3/1996 | C08K/5/18 |
| EP | 0 775 441 | 5/1997 | |
| EP | 0 824 318 | 2/1998 | |
| EP | 0 916 262 | 5/1999 | |
| EP | 0 925 717 A1 | 6/1999 | |
| EP | 1 043 425 | 4/2000 | |
| EP | 1 036 531 A1 | 9/2000 | |
| FR | 1 331 007 | 5/1963 | |
| FR | 2 776 812 | 10/1999 | |
| GB | 1 236 343 | 6/1971 | |
| GB | 1 335 029 | 10/1973 | |
| GB | 1 376 223 | 12/1974 | |
| GB | 2 066 665 A | 6/1979 | |
| GB | 2 046 577 | 11/1980 | |
| GB | 2 115 696 | 9/1983 | |
| GB | 2 150 834 A | 7/1985 | |
| GB | 2 166 653 A | 5/1986 | |
| GB | 2 217 981 A | 11/1989 | |
| GB | 2 151 926 | 7/1994 | |
| GB | WO 96/04786 | 2/1996 | |
| JP | 56 09 0004 | 7/1981 | |
| JP | 63101301 | 6/1988 | |
| JP | 58180575 | 10/1989 | |
| JP | 2 048 507 | 2/1990 | |
| JP | 08284063 | 10/1996 | |
| JP | 08332154 | 12/1996 | |
| WO | 81/00051 | 1/1981 | |
| WO | 85/03275 | 8/1985 | |
| WO | 90/04550 | 5/1990 | |
| WO | WO 93/00580 | 1/1993 | |
| WO | 93/00580 | 1/1993 | |
| WO | 94/12072 | 6/1994 | |
| WO | WO 96/32843 | 10/1996 | |
| WO | WO 00/74490 | 12/2000 | |
| WO | 00/74490 | 12/2000 | |
| WO | WO 0104548 | 1/2001 | |
| WO | WO 01/97617 A1 | 12/2001 | |
| WO | 02/07512 A1 | 1/2002 | |
| WO | WO 0220259 | 3/2002 | |
| ZA | 711214 | 2/1971 | |

OTHER PUBLICATIONS

International Search Report dated Nov. 10, 2002, International Application No. PCT/US02/28413.

International Search Report dated Nov. 12, 2002, International Application No. PCT/US02/28412.

International Search Report dated Nov. 19, 2002, International Application No. PCT/US02/28526.

International Search Report dated Jan. 3, 2003, International Application No. PCT/US02/28422.

International Search Report dated Jan. 10, 2003, International Application No. PCT/US02/28414.

International Search Report dated Jan. 10, 2003, International Application No. PCT/US02/28459.

International Search Report dated Jan. 14, 2003, International Application No. PCT/US02/28456.

International Search Report dated Oct. 20, 2000 Application No. PCT/US00/15205.

100:169902 Abstract of Hirano et al. 665 Japan Eisei Dobutsu (1983), 34(4), 263–8.

Chicago Stationers Incorporated 2003 Catalog, Chicago, Illinois, pp 600–601.

Written Opinion, Appl. No. PCT/US02/28526 dated Sep. 18, 2003.

International Search Report, Appl. No. PCT/US2004/017671 dated Sep. 13, 2004.

Written Opinion, Appl. No. PCT/US2004/017671 dated Sep. 13, 2004.

\* cited by examiner

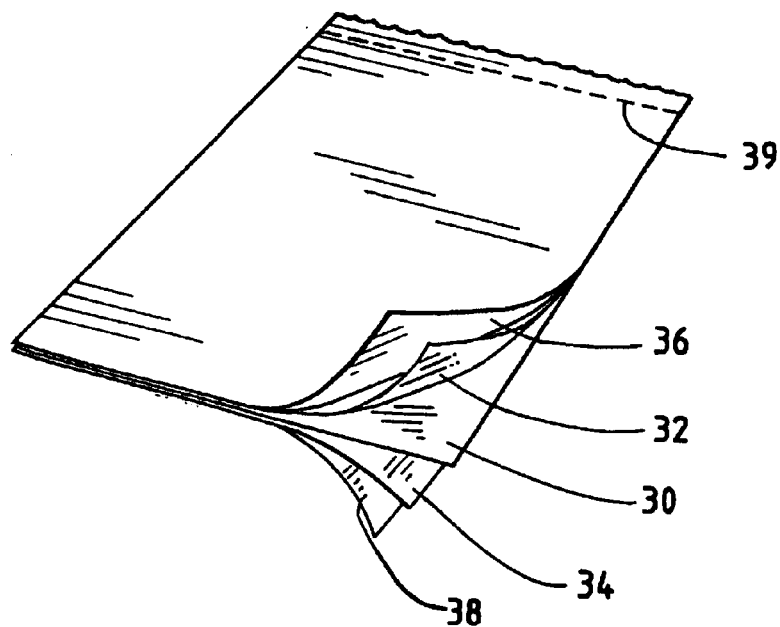
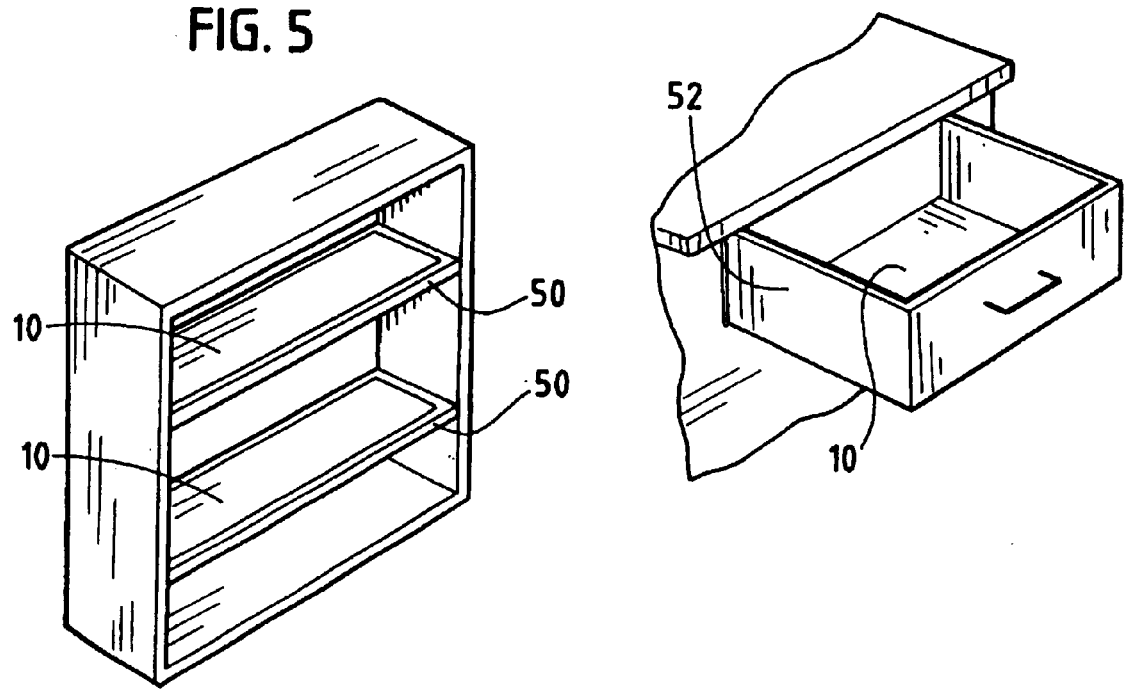

FILM MATERIAL

TECHNICAL FIELD

The present invention relates generally to films, and more particularly to a film material.

BACKGROUND ART

A web or sheet of material is often used to protect a surface and/or one or more items that may be disposed on the web or sheet. For example, paper has been used for many years to line shelves, drawers and other surfaces of articles.

The paper may be plain (i.e., uncoated), coated and/or adhesive-backed. Paper or other material has also been used as placemats or as a table covering.

Another example of the use of a web or sheet is as a protective covering on other, larger structures, such as a dropcloth on a floor or a liner in a trunk of a car or on a bed of a truck. These products typically must be sufficiently durable to withstand foot traffic and/or other forms of abuse, although less durable materials (e.g., paper) may be used as temporary protective coverings.

Mix U.S. Pat. No. 1,151,895 discloses a sanitary kneading board wherein a quantity of parchment paper is unwound from a roll and placed atop the board to completely cover the surface thereof. Similar arrangements are disclosed in Johnson U.S. Pat. No. 1,952,375 and Hoel U.S. Pat. No. 2,369,898, although the wax paper is used instead of parchment paper in the latter.

Pollock U.S. Pat. No. 5,193,793 discloses a mixing board wherein a plurality of stacked plastic sheets are disposed on a top surface thereof. Each of the plastic sheets has a backing of pressure sensitive adhesive binding the sheets together. A user may mix a compound on a top sheet and may thereafter peel off the top sheet and dispose of same so that a clean surface is provided for subsequent use.

A number of arrangements have been developed wherein an electrostatically charged sheet is used to secure an article to a surface. For example, Henley U.S. Pat. No. 5,970,638 discloses a transparent electrostatic vinyl sheet and a cover film wherein an object, such as a dried and pressed flower, is tightly sealed between the vinyl sheet and the cover film to create a sealed ornament. The sealed ornament may be applied to a non-porous surface and the electrostatic film maintains the ornament in position thereon. Other arrangements utilizing electrostatic sheets to mount objects are disclosed in Arbisi U.S. Pat. No. 5,826,851, Baryla U.S. Pat. No. 4,741,119, Saetre U.S. Pat. No. 5,102,171 and Rubino U.S. Pat. No. 4,992,121.

Peck U.S. Pat. No. 5,899,010 discloses a reusable banner system including a sheet of plastic material and a plurality of flexible static cling vinyl indicia that may be placed on the sheet of plastic material to form a message. The indicia are maintained in position on the sheet of plastic material by the electrostatic charge carried by the indicia. In an alternate embodiment, the sheet of plastic material carries an electrostatic charge and the indicia are made of nonporous plastic.

Stonehouse U.S. Pat. No. 5,010,671 discloses a flip chart comprising at least two sheets disposed in overlying relationship. The sheets are electrically charged and are releasably securable to a surface by static cling. The sheets are adapted for removable marking thereon by a felt pen and are retained on a backing board by staples. Each sheet may be torn from the staples to permit removal of the sheet from the flip chart.

Boyd U.S. Pat. No. 5,207,581 discloses a writing apparatus including flexible electret film that is capable of being erasably written upon by a dry erase marker. The apparatus includes a roll of electret film disposed in a receptacle, brackets for mounting the receptacle to a wall or flip chart stand and a cutter for separating the film into sheets.

Cooledge et al. U.S. Pat. No. 5,258,214 discloses a thermoplastic film material having a preprinted image thereon and provided with a static electrical charge for securing the film to a surface. The material may be packaged as sheets or in roll form with perforations to permit separation thereof.

SUMMARY OF THE INVENTION

In accordance with one aspect of the present invention, a material includes a first film layer that carries an electric charge, a second film layer secured to the first film layer to form a pocket and a volatile substance disposed in the pocket.

According to a further aspect of the present invention, a material includes a first film layer that carries an electric charge, a second film layer secured to the first film layer to form a pocket wherein the second film layer has an opening extending therethrough and a volatile substance disposed in the pocket. Other aspects and advantages of the present invention will become apparent upon consideration of the following detailed description.

BRIEF DESCRIPTION OF THE DRAWINGS

FIG. 4 comprises an isometric view of a multilayer polymer film according to the present invention;

FIGS. 5 and 6 comprise isometric views of shelves and a drawer, respectively, that are lined with a film material according to the present invention;

DESCRIPTION OF THE PREFERRED EMBODIMENTS

Figure 1:
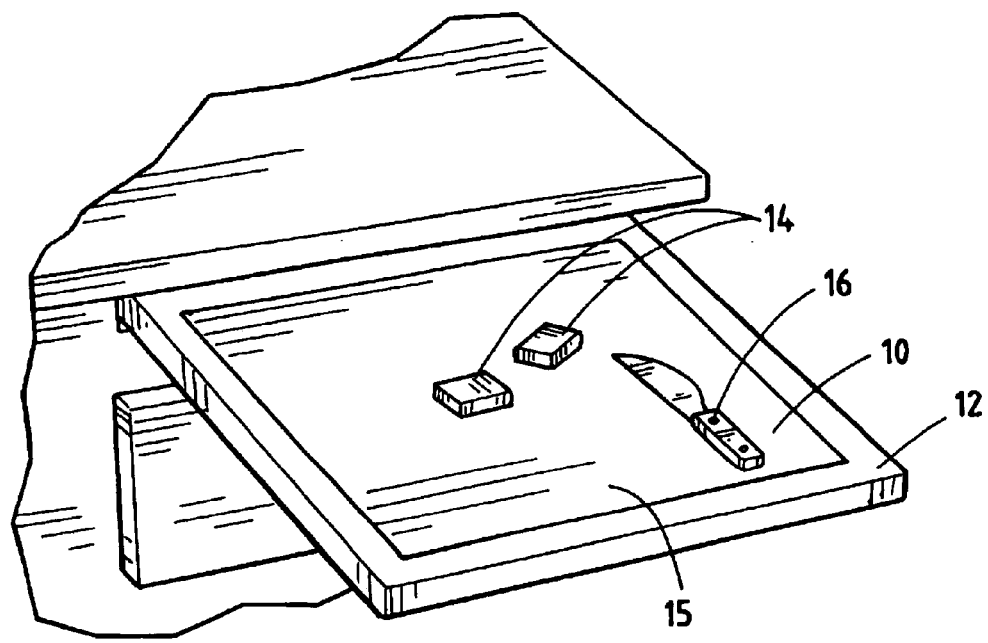
FIG. 1 comprises an isometric view of a cutting board having a film material according to the present invention disposed thereon.

Referring now to FIG. 1, a film material 10 according to the present invention is illustrated. In accordance with the preferred embodiment, the film material 10 comprises a polymer or other material that is readily capable of accepting and retaining an electric charge. Also preferably, the material is inexpensive so that it may be used once and recycled or discarded. Still further, the film material 10 is sufficiently durable to resist contact by a knife or other utensil and has adequate resilience to resist cracking when flexed. Still further in accordance with the preferred embodiment, the material comprises a plastic film that is liquid impermeable and preferably approved by the FDA for contact with food.

The thickness of the film material 10 is in a range encompassing up to approximately 8 mils, with a range of approximately 0.5 to approximately 5 mils being preferred, the range of approximately 1 to approximately 4 mils being more preferred and the range of approximately 1.5 to approximately 3 mils being most preferred. Further, the film material is preferably charged by application of a positive or negative electric field of at least approximately 15,000 volts thereto at an approximate distance of between ½ inch and 1 inch, with at least approximately 20,000 applied volts being more preferred and at least approximately 30,000 applied volts being most preferred substantially at a distance of ¾ inch. If desired, the material 10 may be exposed to a positive electric field on one side thereof and a negative electric field on the other side thereof wherein the magnitudes of the applied fields are as noted above. In alternate embodiments, the film material 10 is exposed to the same polarity fields on opposite sides thereof (i.e., a first side of the material 10 is exposed to a first positive field and a second side of the material 10 is exposed to a second positive field or first and second sides of the material 10 are exposed to first and second negative fields, respectively.). In addition, the material 10 preferably retains a charge sufficient to develop an electric field at a voltage substantially equal to at least approximately 1500 volts at a specified time after charging of the material, such as three months or more. More preferably, the material retains sufficient charge to develop an electric field at a voltage of at least approximately 2500 volts, and most preferably at least approximately 3500 volts, at least for the period of time between the initial application of charge to the film material 10 and the longest anticipated time to use by the consumer.

Figure 1A:
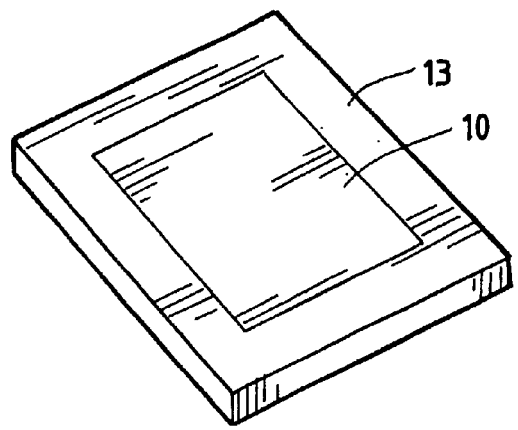
FIG. 1A comprises an isometric view of a support surface having a film material according to the present invention disposed thereon.

The film material 10 of FIG. 1 is placed atop a support surface 12, shown as a cutting board, and one or more items 14 are placed on an upper surface 15 of the film material 10 and are processed. As seen in FIG. 1A, if desired, the film material may instead be disposed on a different structure 13, such as a countertop, a table, a tray, etc. . . . Referring again to FIG. 1, in accordance with one embodiment, the items 14 comprise food items that are cut with a knife 16 and/or otherwise manipulated (such as during mixing, kneading, chopping, and the like) while on the film material 10. The film material 10 prevents the transmission of juices and other materials released from the food item(s) 14, including bacteria, from the upper surface 15 to the support surface 12. The film material 10 also prevents the transmission of materials and bacteria from the support surface 12 to the upper surface 15 of the film material 10, and hence, contamination of the food item(s) 14 is avoided. If desired, the film material 10 may optionally include one or more antimicrobial and/or bactericidal components that limit germ and/or bacterial activity on at least the upper surface 15.

The support surface is preferably of a suitable material and construction to provide static attraction with the film material 10. Ideally, the support surface provides sufficient support to the film material and the item(s) 14 to permit safe and efficient processing thereof. When processing of the food item(s) 14 is complete, the film may be removed from the support surface 12 and may be recycled or disposed of, preferably after first folding and/or wadding the film material 12 in such a manner so as to capture food particles and juices therein. Also preferably, the charge carried by the film material 10 is of a magnitude such that the film material 10 is restrained against significant movement during processing of the item(s) 14 thereon, yet easy release of the film material 10 from the support surface 12 can be accomplished, when desired. Specifically, the film material preferably exhibits a moderate to high resistance to shear forces but a relatively lower resistance to a peeling force. Also, the resistance to shear forces is preferably not so great as to prevent any lateral adjustment of the position of the material 10 once it is placed on a surface. Thus, the material 10 can be placed on a surface and the position thereof may be adjusted, and thereafter the material 10 is retained in position by the electrical charge carried by the material 10. As a result, the material 10 can be written on or items can be processed and/or moved on the material 10 without substantial lateral movement of the material 10, yet the material can be readily repositioned or peeled from the underlying surface, when desired.

The film material preferably comprises a monolayer or multilayer structure of any suitable polymer material(s) formed into a film, such as an olefin (e.g., polypropylene or polyethylene), nylon, PET, Teflon, or any other family of chemicals capable of being formed into a film and/or may comprise non-oriented, oriented or biaxially oriented materials. The film alternatively may comprise combinations of such materials in different layers that are coextruded or laminated or otherwise joined together.

Figure 2:
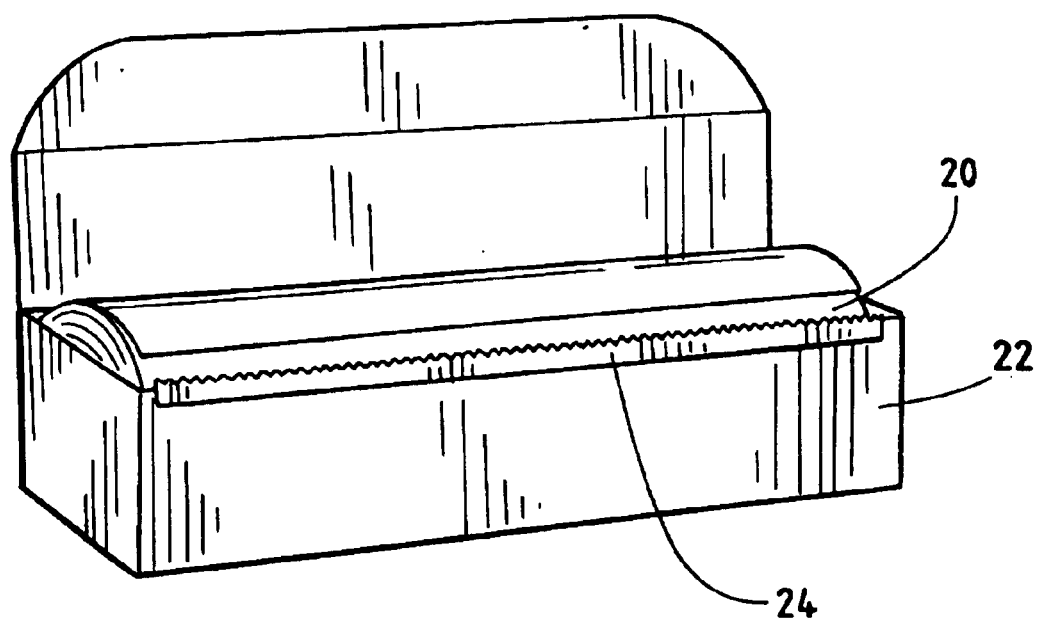
FIG. 2 comprises an isometric view of a container in combination with a roll of film material according to the present invention.

In the preferred embodiment of the invention, the film material 10 is extruded into a web and wound onto one or more large master rolls. The film material 10 is thereafter unwound from the master roll(s), passed through any commercially available electrostatic charging machine and immediately thereafter formed into individual user rolls. Each roll is supplied to the end user, who preferably cuts or otherwise trims the material to a desired size and/or shape. As seen in FIG. 2, a roll 20 of the film material 10 is supplied in a box 22 or other container and a cutter bar 24 is mounted on the box 22 to permit the user to trim the material 10 into a sheet of desired size. Alternatively, the material 10 may be supplied to the end user as precut sheets in a box or other container. Still further, the material 10 may be perforated to allow a user to easily tear the material 10 into sheets.

Figure 9:
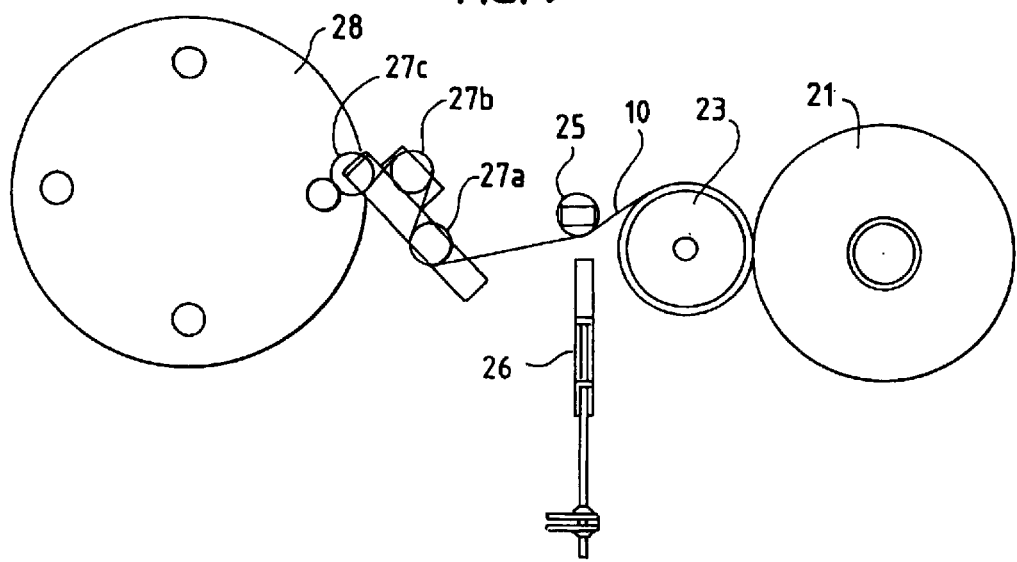
FIG. 9 is a diagrammatic plan view of apparatus for charging and winding film material onto individual rolls.

FIG. 9 illustrates the foregoing procedure in greater detail wherein film material 10 stored on a large master roll 21 is unwound therefrom by a driven bed roller 23 and passed over a further roller 25 disposed adjacent a charging machine 26. Preferably, the charging machine 26 comprises a Tetra charging bar sold by Simco of Hatfield, Pa., which preferably delivers a positive charge to the film material 10. Also preferably, the film material travels past the charging machine 26 at a line speed of approximately 800 feet per minute, although higher or lower travel speeds could alternatively be used. The charged film material 10 then passes over further rollers 27a, 27b and 27c and is wound onto individual rolls carried by a rotatable turret 28. Preferably, the rollers 25, 27a and 27c are grounded to a machine frame by brushes or other devices and the rollers 27a–27c are insulated by a Teflon coating. In addition, the roller 25 is preferably coated by an electrically non-conductive industrial hard coating.

The foregoing manufacturing technique results in less handling by manufacturing personnel, as compared to a technique wherein the extruded film is wound onto a large master roll, and the master roll is thereafter electrostatically charged in bulk and the charged film is unwound from the master roll and wound onto individual rolls or formed into individual sheets. This reduction in handling results in better charge retention and improved film quality. Also, the foregoing technique results in production of amounts of ozone that are within acceptable limits.

If desired, the film material 10 may be charged while in the semi-molten state, thereby forming an electret having internal charges in the film structure. Specifically, this aspect of the present invention comprehends the steps of forming a molten thermoplastic material into a web, electrically charging the web while the web is at a temperature substantially at or above a solidification temperature thereof, cooling the web below the solidification temperature thereof after charging and winding the web into individual rolls immediately following the cooling step. The web may be of single layer or multi-layer construction, wherein the latter may be accomplished by coextrusion techniques. Preferably, the method comprehends the use of a charging machine similar or identical to the charging machine 26 described above which is located downstream of an extrusion die that extrudes the thermoplastic web. After charging, the semi-molten material is allowed to cool, either by exposure to ambient conditions or by active chilling by a chiller roll. One or both outer surfaces of the web may be corona-treated to permit marking by a marking device. Thereafter, the cooled web is preferably immediately rolled onto individual user rolls and packaged.

During charging, the material 10 is exposed to a positive or negative electric field preferably when the film temperature is just greater than the glass transition temperature TG for the material 10. Also preferably, the semi-molten material is exposed to at least approximately 15,000–17,000 volts at an approximate distance of between ½ inch and 1 inch, with at least approximately 20,000 applied volts being more preferred and at least approximately 30,000 applied volts being most preferred substantially at a distance of ¾ inch. If desired, the material 10 may be exposed to a positive electric field on one side thereof and a negative electric field on the other side thereof wherein the magnitudes of the applied fields are as noted above. In alternate embodiments, the film material 10 is exposed to the same polarity fields on opposite sides thereof, i.e., a first side of the material 10 is exposed to a first positive field and a second side of the material is exposed to a second positive field or first and second sides of the material are exposed to first and second negative fields, respectively.

This technique, as opposed to the electrostatic charging described above that creates surface charges in the material 10, results in a more stable retention of electric charge over time and with exposure to ambient conditions. Also if desired, the film may initially be charged when partially molten and thereafter may be passed through a charging machine after solidification of the material 10 just before winding into individual rolls as noted above to obtain a product with a combination of internal and surface charges.

Regardless of whether the film is charged only when partially molten or charged before and after solidification, the resulting film preferably has at least the electrical charge retention characteristics specified above. That is, the resulting film material 10 preferably retains a charge sufficient to develop an electric field at a voltage substantially equal to at least approximately 1500 volts at a specified time after charging of the material, such as three months or more. More preferably, the material 10 retains sufficient charge to develop an electric field at a voltage of at least approximately 2500 volts, and most preferably at least approximately 3500 volts, at least for the period of time between the initial application of charge to the film material 10 and the longest anticipated time to use by the consumer.

Figure 3:
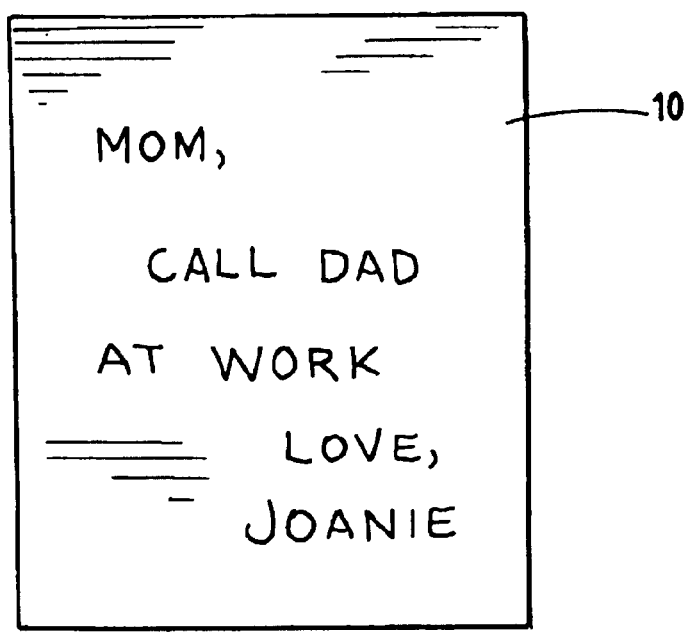
FIG. 3 comprises a plan view of a film according to the present invention with markings thereon created by a dry-erase marker.

The film material 10 may be colorless or pigmented and may be transparent, translucent or opaque, as desired. Referring to FIG. 4, according to one embodiment, the material 10 may comprise a multilayer coextruded or laminated structure comprising a cavitated center layer 30 of a polypropylene sold under the trademark OPPALYTE® by Exxon Mobil Corp., first and second intermediate layers 32, 34 of polypropylene modified by the addition of titanium dioxide thereto to obtain a white pigmentation and top and bottom outer layers 36, 38. In this embodiment, the top outer layer 36 is preferably polypropylene that has been corona-treated to allow marking with either a permanent marking device or to allow removable marking with a dry-erase marker. Further, the bottom outer layer 38 is preferably polypropylene modified by the addition of any known material that facilitates cold sealing of the film material 10. If desired the bottom outer layer 38 could be corona-treated to allow permanent or removable marking thereon as noted above. In addition, the resulting film may be laminated to another structure, such as a substrate. Thus, as seen in FIG. 3, the material can be cut or severed to a desired size, mounted on a surface and used as a portable dry-erase board. Marking of the material can be undertaken at any time, for example, before severing, after severing but before mounting or after mounting.

Still further, the material 10 may be printed on one or more surfaces thereof. Also, the film material 10 may be perforated at one or more locations 39 (FIG. 4) to permit tearing into sheets without the need for a cutter bar.

According to a further embodiment, the film material 10 is identical to the embodiment illustrated in FIG. 4 except that the outer layers 36 and 38 are omitted. In addition, the three layers are coextruded or laminated and each layer comprises 187, 155LLG102 BOPP manufactured by Exxon Mobil Corp., wherein the layers are not modified by pigment and are not cavitated to obtain a clear product.

If desired, the material 10 need not be electrically charged.

INDUSTRIAL APPLICABILITY

The present invention is not limited to the concept of providing a material that may be used as noted above. For example, the material 10 may be used to line one or more shelves 50 or drawers 52 (FIGS. 5 and 6) and items may be placed and/or processed thereon, or the material 10 may be used to cover and/or protect the surfaces of other furniture, articles and other support surfaces so that one or more items may be placed and/or processed thereon (such as house plants, picture frames or the like). Items other than food, e.g., items used in crafts, may be supported on the material 10 for processing. Alternatively, the material may be used as a dropcloth and/or placemats or in another application, such as in a refrigerator or microwave, where protection of a support surface is desired. Still further, the material 10 may be used as a cover for a bowl, cup or other receptacle, or may be used to serve as a splash guard for one or more surfaces in a microwave oven or refrigerator, or may be used like masking tape to keep paint from being applied from areas that are to remain unpainted. Another use is to retain an item on place on a windowpane or other object by sandwiching the object between the film material 10 and the windowpane or other object. The surface upon which the material 10 is placed may be continuous or discontinuous (an example of the latter would be a tile floor). In addition, the surface may be hard or soft, and need not have a homogenous composition or exhibit homogeneous physical characteristics.

As further alternatives, the film material 10 may include one or more openings or apertures therethrough and/or the material 10 may include pigmented and non-pigmented areas and/or electrically-charged and non-charged areas, as desired. Thus, for example, a rectangular piece of film material 10 may include an outer portion comprising a frame which is electrostatically charged and which is corona treated to accept removable or permanent marking thereon and a central portion which is clear or which has an opening therethrough. The material of the central portion (if any) may be electrostatically charged or uncharged. The resulting product is particularly suited to hold a photograph, drawing, painting, greeting card, or other object to a windowpane or other substrate (vertical or non-vertical) such that the photograph, drawing, etc. . . . is visible through or at the central portion. In the case of applications where the film material 10 is to hold an object to a vertical surface and where either portions of or the entire sheet (including any central portion) is electrically charged, the film material 10 preferably (although not necessarily) carries an electric charge sufficient to enable the material to hold a weight of a separate object at least equal to the weight of the film material 10. In alternate embodiments, the charge is sufficient to allow the material to hold a weight of a separate object greater than the weight of the film material, for example, a weight at least equal to three times the weight of the film material.

According to still further alternative, a sheet of the film material 10 may include outer margins that retain electric charge, such as an electrostatic charge. The sheet may be folded on itself such that portions of the outer margins are placed into contact with one another, thereby forming a pocket that may enclose an object. If desired, the entire sheet may carry an electric charge or portions of the sheet other than the margins may carry an electric charge. One or more surfaces may optionally be treated as noted above to permit permanent or removable marking of such surface(s) by a marking device, such as a dry erase marker. As in the previous embodiments, the film material prevents the transmission of bacteria and fluids between the surfaces of the material.

Yet another embodiment of the present application comprehends an electrically charged sheet of film material as described above in connection with any of the previous embodiments, wherein the film material 10 is treated and/or modified in some fashion to apply a desired substance having a desired property thereto. For example, a quantity of electrostatically charged film having a surface that may be treated so as to be capable of being marked by a dry erase marker may further have one or more portions coated with a volatile substance, such as an insecticide, a bactericide, an antimicrobial agent and/or a fragrance. The film may be liquid impermeable and may be trimmed to a desired size and placed in contact with a surface (such as a top surface, undersurface or side surface of a shelf, table, drawer, etc. . . . ) such that the film is attracted to and retained on the surface. The substance thereafter volatilizes to release same into the ambient surroundings. Optionally, an item may be processed on the film, provided that the item is not adversely affected by the volatile substance.

If desired, the substance may be a substantially nonvolatile liquid, such as an oil, or a solid material or article, such as a printed sheet of paper, fabric, plastic, etc. . . . In this case, the substance may be irremovably secured to the film material 10, or the substance may be removable therefrom. In the latter case, the film material 10 may serve as a transfer carrier that carries the substance until the film material 10 is applied to a surface, whereupon the substance is transferred to the surface and is retained thereon by any suitable mechanism. Such mechanism may include electrostatic attraction resulting from electric charge transferred to the substance by the film material 10. An alternative mechanism may comprise adhesion resulting from making one or more surfaces of the substance sticky. In any event, the film material 10 may be peeled from the surface, leaving at least some quantity of the substance on the surface.

Figure 7:
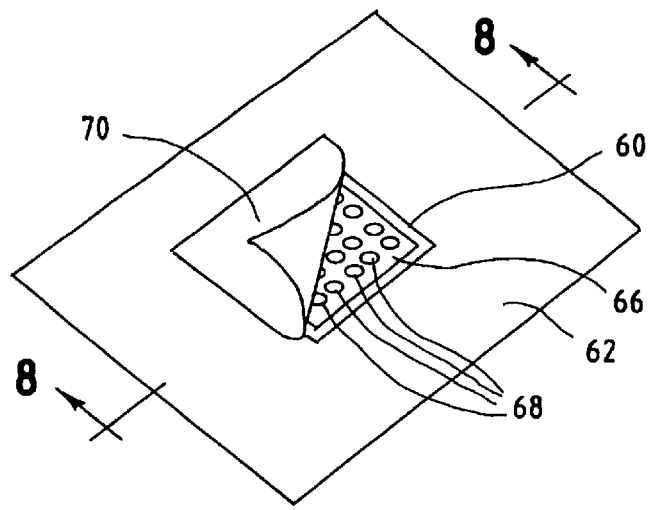
FIG. 7 is an isometric view of a film with a pouch containing a pad or other member impregnated with a substance.
Figure 8:
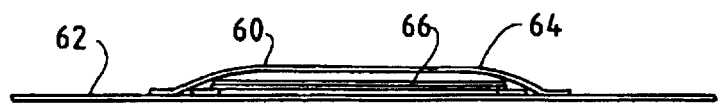
FIG. 8 is a sectional view taken generally along the lines 8—8 of FIG. 7.

Alternatively, a volatile material or other substance or article may be retained in or by a structure carried by or secured to the film. For example, as seen in FIGS. 7 and 8, a layer 60 of a first film may be disposed atop and secured to a layer 62 of a second film that carries an electric charge as noted above to create a pocket 64. The layers 60 and 62 may be made of any of the materials described above or any other material and the layer 60 may be secured to the layer 62 in any known manner, such as by heat sealing, adhesive bonding, coextrusion, or the like. A pad 66 impregnated with a desired substance, such as a fragrance, insecticide or any other substance as described herein, may be disposed in the pocket 64. The pad 66 may comprise a gel disposed in an envelope formed by two layers of vapor permeable material that are secured to one another by any suitable means. One or both of the layers 60, 62 may be vapor permeable and/or one or more openings or apertures 68 may be provided in the first and/or second films to permit vapor communication between the ambient surroundings and the pocket 64. The holes 68 may initially be covered by one or more removable adhesive strips 70 (shown only in FIG. 7) or other members. The resulting product may be placed on any desired object at a desired position (including a top surface, side surface or an undersurface of the object) and is retained thereon by the electric charge carried by the film. The adhesive strip(s) 70 may then be removed to expose the substance to the ambient surroundings. The substance, if volatile, will thereafter evaporate and spread in vapor form to the surroundings. If desired, the pad 66 may be replaced by a different carrier, such as a fibrous pad or other material containing or impregnated with a desired substance.

A still further alternative is a design whereby a pouch is formed of a material (whether one of the materials described above or any other material), either by folding the material upon itself or by securing two or more pieces of the same or dissimilar materials together to form one more pockets, and securing the pouch by any suitable means (e.g., heat sealing, adhesive, coextrusion, co-lamination or the like) to a section of a film that carries electric charge as described above. One or more objects may be disposed in the pocket(s), including a pad impregnated with a substance as described above. The material of the pouch may be vapor permeable an/or may include one or more openings extending therethrough. One or more holes covered by removable members may be provided as in the preceding embodiment. The resulting product may be placed and used as described in the preceding embodiment to expose the impregnated substance to ambient surroundings.

In any of the foregoing embodiments, the desired substance may be a repellant and/or toxic to one or more undesirable organisms, creatures, etc . . . Thus, the desired substance may comprise an antimicrobial composition, an insecticide, a bactericide, a herbicide, an animal repellant, or the like. Alternatively, the desired substance may be an attractant (such as a fragrance as noted above) or a substance that encourages growth or multiplication of one or more organisms. Of particular interest in this regard are scents and other air quality control active ingredients and insect control ingredients, including insecticides, repellants and other insect behavioral and/or developmental modification ingredients. Any of these substances can be applied to the film material 10 by any suitable means in addition to those described above, such as a composition which is printed directly on the film material 10, a woven or non-woven fabric or other material impregnated with the substance and laminated or otherwise joined to the material 10, etc . . . . The substance may therefore be dispensed without messy and/or sticky residue. One example of such a substance release arrangement is a 10 inch by 10 inch 2 mil polypropylene film with 100 milligrams of transfluthrin or other insecticide or active applied thereto. Other insecticidal compositions may instead be used in this manner. The resulting material may be supplied in sheet or roll form, and in the latter case, the material may be torn or cut into a desired size by a cutter bar or other implement as described above. The material may alternatively be perforated to allow ready separation into individual sheets, also as noted above. The material may be placed on a substantially horizontal undersurface or any other surface of an object, such as a tray, table countertop, drawer, shelf, a substantially vertical surface, etc . . . , whereupon the volatile substance volatilizes to release an active ingredient into the surrounding environment.

If desired, any of the foregoing embodiments may be adapted to be utilized with a heater that heats the film material 10 either to initiate or accelerate the release of the substance into the surrounding atmosphere. A fan may instead or in addition be used to initiate/accelerate substance release.

Figure 10:
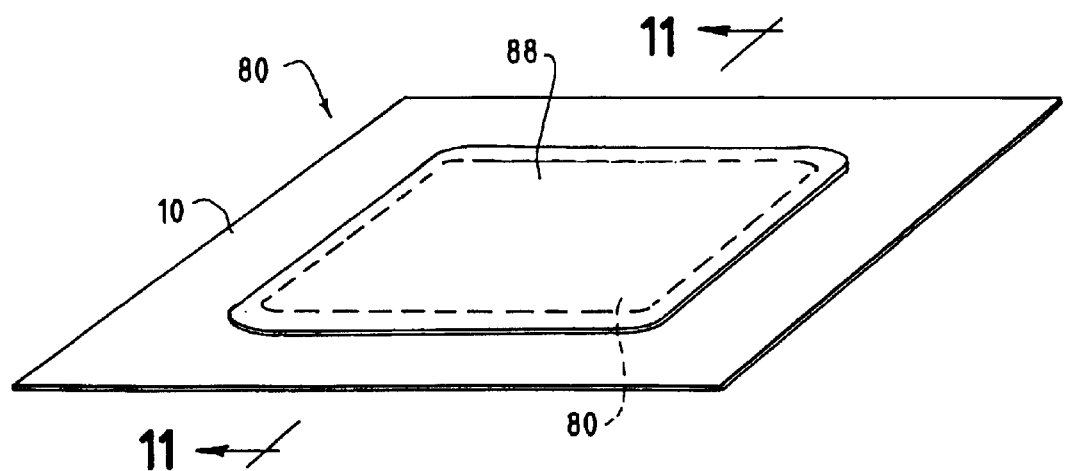
FIG. 10 is an isometric view of a film material with a multi-compartment structure retained thereon.
Figure 11:
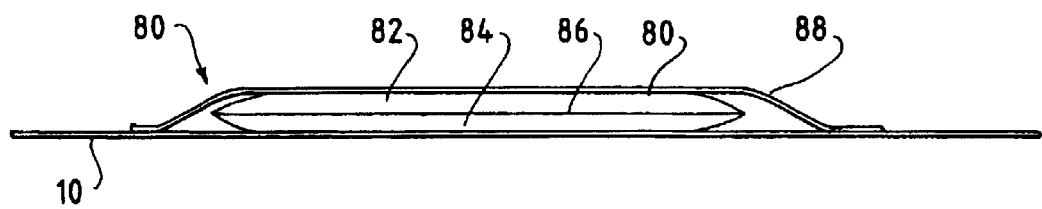
FIG. 11 is a sectional view taken generally along the lines 11—11 of FIG. 10.

Yet another embodiment comprehends a structure including two or more compartments or pockets secured to the electrically charged film material 10. For example, as seen in FIGS. 10 and 11, a multi-compartment arrangement 80 includes at least first and second compartments or pockets 82, 84 separated by a rupturable intermediate wall 86. The compartments 82, 84 are captured between a base layer comprising a section of the film material 10 and a cover layer 88 that is secured by any suitable means to the base layer. In the case of a structure having more than two compartments, each compartment is separated from adjacent compartment(s) by one or more rupturable walls. A chemical composition is disposed in each compartment and the rupturable walls may be selectively ruptured by physical manipulation to mix the chemicals and thereby initiate a desired chemical reaction. The structure may be retained on any surface by the charge carried by the film material 10. Thus, for example, a cold pack may be provided by a multi-compartment structure wherein the components of the cold pack are separated before use by rupturable walls. A user may rupture the walls when the cold pack is to be used such that the chemicals are mixed and the chilling process is initiated, whereupon the cold pack may be applied to an affected area of a person's body. The cold pack is advantageously retained at the affected area by the charge carried by the film material 10. Other similar arrangements can be envisioned whereby chemicals are selectively mixed to produce heat, light, smoke or other byproduct, and the structure is retained on a surface by the electric charge carried by the film material 10.

Any of the features of one of the embodiments disclosed above can be combined with one or more features of one or more other embodiments disclosed above. Thus, for example, an electrically charged sheet of polymer material as described above having the above-noted charge retention and holding characteristics may be coated or impregnated with a volatile substance, such as an insecticide or fragrance, and, if desired, one or both surfaces of the sheet may be treated to permit permanent or removable marking of such surface(s) by a marking device, such as a dry erase marker. The material may be supplied in sheet or roll form, and in the latter case, the material may be torn or cut into a desired size by a cutter bar or other implement as described above. The material may alternatively be perforated to allow ready separation into individual sheets, also as noted above.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A material, comprising:
   a first film layer that carries an electric charge;
   a second film layer secured to the first film layer to form a pocket; and
   a volatile substance disposed in the pocket;
   wherein the first film layer is electrostatically attractable to a surface.

2. The material of claim 1, wherein the first and second film layers are liquid impermeable.

3. The material of claim 1, wherein the second film layer is secured to the first film layer by heat sealing.

4. The material of claim 1, wherein the films are made of a polymer.

5. The material of claim 4, wherein the polymer is polypropylene.

6. The material of claim 1, wherein the material is electrostatically held on a substantially vertical surface.

7. The material of claim 1, wherein the volatile substance is a fragrance.

* * * * *